United States Patent [19]

Tanaka et al.

[11] Patent Number: 5,296,507

[45] Date of Patent: Mar. 22, 1994

[54] TREATMENT OF CERBROVASCULAR DISORDERS

[75] Inventors: Yoshiaki Tanaka; Naomi Kobayashi; Tadashi Kurimoto, all of Saitama; Yugo Ikeda, Tokyo, all of Japan

[73] Assignee: H.Lundbeck A/S, Copenhagen-Valby, Denmark

[21] Appl. No.: 1,571

[22] Filed: Jan. 6, 1993

Related U.S. Application Data

[63] Continuation of Ser. No. 742,907, Aug. 9, 1991, abandoned.

[30] Foreign Application Priority Data

Sep. 6, 1990 [DK] Denmark .......................... 2132/90

[51] Int. Cl.$^5$ ............................................. A61K 31/36
[52] U.S. Cl. ........................................................ 514/465
[58] Field of Search ......................................... 514/465

[56] References Cited

PUBLICATIONS

Folia Haematol. Leipzig, vol. 115, No. 4, 1988, pp. 475–478, Heptinstall, et al., "How can we inhibit 5-H-T-induced platelet aggregation and why should we bother?"
Archives of Pharmacology, vol. 334, No. 4, Dec. 1986, Springer International, pp. 341–345, Bevan, et al., "Effects of combinations of 5-hydroxytryptamine receptor antagonists on 5-HT-induced human platelet aggregation".
The Journal of Biological Chemistry, vol. 260, No. 12, Jun. 25, 1985, pp. 7603–7606, The American Soc. of Biological Chemists US, Chaffoy De Courcelles, et al., "Evidence that phospholipid turnover is the signal transducing system . . . ".
Nord. Psykiatr. Tidsskr., vol. 41, No. 6, 1987, pp. 423–429, S. E. Nyth, et al., "Behandling med citalopram vid demens. Normalisering av DST".
Drugs of the Future, vol. 15, No. 6, Jun. 1990, editor J. R. Prous et al., p. 618, "Citalopram".
The British Journal of Psychiatry, vol. 157, Dec. 1990, pp. 894–901, The Royal College of Psychiatrists, Nyth, et al., "The clinical efficacy of citalopram in treatment of emotional disturbances in dementia disorders. A nordic multicentre study".
Psychopharmacology, supplement to vol. 96, 1988, Abstracts of the XVIth C.I.N.P. Congress, Aug. 15–19, 1988, Munich, p. 45, Abstract No. TU24.04, Springer International, Gottfries, "Dementia disorders and depression in the elderly. Biochemical aspects".
Nyth, A. L. et al., "The effect of citalopram in dementia disorders. A Scandinavian multicentre study", Abstract of the XVIth C.I.N.P. Congress, Munich, Aug. 15–19, 1988.
Nyth, A. L., et al. ECNP Abstract 1989, Sweden, 79. (Appendix C) Brane, "The GBS scale: a new rating scale for dementia syndromes", Nort Psykiatr. Tidssk, 1986, 40, 125–134.
Nyth, et al., Acta Psychiatr. Scand., 1992, 86, 138–145.

*Primary Examiner*—S. J. Friedman
*Attorney, Agent, or Firm*—Gordon W. Hueschen

[57] ABSTRACT

A method for the treatment of dementia and cerebrovascular disorders and for inhibiting platelet aggregation in patients in need thereof comprising the step of administering a therapeutically effective amount of a 1-[3-(dimethylamino)propyl]-1-phenylphthalane of the general formula

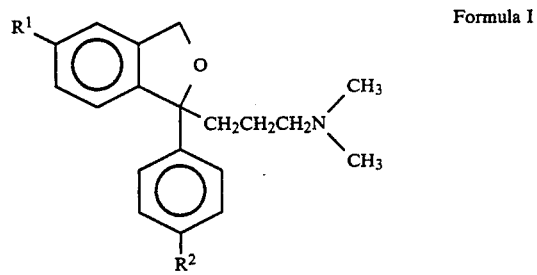

Formula I wherein $R^1$ and $R^2$ each are selected from the group consisting of halogen, trifluoromethyl, cyano and R—CO—, wherein R is an alkyl radical, or a pharmaceutically-acceptable acid addition salt thereof, is described.

7 Claims, No Drawings

TREATMENT OF CERBROVASCULAR DISORDERS

This is a continuation of application Ser. No. 07/742,907, filed Aug. 9, 1991, now abandoned.

The present invention relates to the use of a class of 1-[3-(dimethylamino)propyl]-1-phenylphthalanes for the treatment of dementia and cerebrovascular disorders and for inhibiting platelet aggregation, and to the production of medicaments or pharmaceutical compositions containing the same for such purposes.

U.S. Pat. No. 4,136,193 relates to 1-[3-(dimethylamino)propyl]-1-phenylphthalanes having the general formula

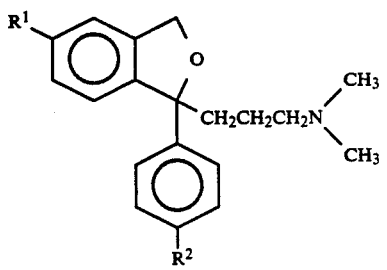

Formula I wherein $R^1$ and $R^2$ each are selected from the group consisting of halogen, trifluoromethyl, cyano and R—CO—, wherein R is an alkyl radical with 1 to 4 C-atoms inclusive, and acid addition salts thereof with pharmaceutically-acceptable acids.

Said compounds are described to be selective, centrally active serotonin (5-hydroxytryptamine; 5-HT) reuptake inhibitors and accordingly to have antidepressant activities. One of the tests used to show such activities was inhibition of $^{14}$C-5-HT uptake in rabbit blood platelets in vitro. The compound of Formula I wherein $R^1$ is a cyano group and $R^2$ is a fluorine atom is the known antidepressant citalopram, the antidepressant activity of which has been reported in several publications, e.g. J. Hyttel, Prog. Neuro-Psychopharmacol. & Biol. Psychiat., 1982, 6, 277–295 and A. Gravem, Acta Psychiatr. Scand., 1987, 75, 478–486. A method for preparation of and intermediates for the preparation of citalopram are described in U.S. Pat. No. 4,650,884 and methods of preparing the individual enantiomers of citalopram are disclosed in U.S. Pat. No. 4,943,590.

Biochemical postmortem investigations of patients with Alzheimer's disease have shown hypofunction of the serotonin nervous system in the brain (D. M. Bowen et al., J. Neurochem., 1983, 41, 266–272). It is also known that depression is one of the major symptoms in Alzheimer's disease, and citalopram has been reported to be effective against depression associated with Alzheimer's disease (C. G. Gottfries, Psychopharmacology, 1988, 96, 45 (Suppl.)). A study of a group of patients with moderate dementia of Alzheimer's type (AD/SDAT) or multi-infarct dementia (MID) has shown significant improvements in emotional lability, motivation, confusion, fear-panic, irritation, reduced mood and restlessness, whereas citalopram did not appear to have effect on intellectual functions (Nyth, A. L. et al. "The effect of citalopram in dementia disorders", presentation at CINP, August 1988; subsequently reported in Nyth, A. L. and Gottfries, C. G., "The clinical efficacy of citalopram in treatment of emotional disturbances in dementia disorders. A nordic multicentre study." Br. J. Psychiat., 1990, 157, 894–901). Later controlled studies showed that treatment with citalopram caused no significant improvement on emotional disturbances in patients with vascular dementia (VD, incl. MID) (Nyth, A. L. et al. "The efficacy of citalopram in treatment of emotional disturbances in dementia disorders", ECNP Abstract 1989, Sweden, 79).

It has also been described that certain 5-HT$_{1A}$ agonists show effect in the treatment of Apoplexia cerebri (Danish Patent Application No 4616/89).

Cerebrovascular disorders, such as ischemia which are triggered by cerebral infarction, cerebral hemorrhage, cerebral arteriosclerosis, subarachnoid hemorrhage, cerebral thrombosis, cerebral embolism, and other diseases are of increasing importance among the population and there is a great demand for effective and safe drugs for the treatment of such disorders and the sequelae of such disorders. A particular problem is dementia not only caused by cerebrovascular disorders but also dementia of other genesis.

Surprisingly, it has now been found that the compounds of the above Formula I effect improvement of cerebrovascular disorders, in particular ischemia, and the brain damage and the impairment of memory functions in connection therewith, and that they show inhibiting action on platelet aggregation. Furthermore, the compounds of the general Formula I have been found to have an anti-amnesic effect and to improve cognitive function in elderly depressed patients having concomitant dementia, i.e. not only dementia of cerebrovascular origin, but also dementia as a result of chronic organic reactions, such as neurodegenerative disorders.

Accordingly, the present invention relates to the use of a compound of the above Formula I for the prevention or treatment of senile dementia and of cerebrovascular disorders and for the inhibition of platelet aggregation, and for the manufacture of medicaments or pharmaceutical compositions for such uses.

Senile dementia may be senile dementia of any genesis such as neurodegenerative, traumatic, cerebrovascular, anoxic, etc, i.e., dementia of Alzheimer's type, multi-infarct dementia or vascular dementia, etc.

Cerebrovascular disorders are brain damages caused by cerebral infarction, cerebral hemorrhage, cerebral arteriosclerosis, subarachnoid hemorrhage, cerebral thrombosis, cerebral embolism, or the like, e.g., ischemia, and the psychological and neurological sequelae of such damages.

The use of the optical isomers of the compounds of general Formula I and their mixtures, including racemic mixtures thereof, is embraced by the invention.

The compound of general Formula I may be used as the free base or as a pharmacologically-acceptable acid addition salt thereof. As acid addition salts such salts formed with organic or inorganic acids may be used. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

An appropriate oral dose of the compound of general Formula I is 1–100 mg/day p.o.

Due to the inhibition of platelet aggregation the medicaments obtained and used in accordance with the invention are useful in the treatment and/or prevention of microcirculation disturbances in the brain resulting from the above cerebral conditioins or from venous or arterial thrombosis, or elsewhere in the body resulting from venous or arterial thrombosis or related conditions.

In view of the beneficial effects on cognitive function and on brain damages and of the platelet aggregation inhibiting effects now found as well as of the known effects on 5-HT uptake, the medicaments obtained and used in accordance with the present invention are useful in the treatment of senile dementia and cerebrovascular disorders, and the sequelae of cerebrovascular disorders such as psychiatric symptoms, e.g., anxiety, depression, loss of memory, hypobulia, restlessness, dementia, hallucinations, delusions, disturbances of conciousness, hypochondriac tendency, insomnia, excitation, garrulity, hyperkinesia, deliriums, and disturbances of orientation, neurological symptoms, e.g., alalia, and hypodynamia, and subjective symptoms, e.g., headache, dizziness, feeling of numbness, feeling of stiffness in the shoulder, feeling of exhaustion and heavy feeling in the head.

Additionally they have the further advantage of a very good safety profile.

A preferred compound of Formula I is citalopram.

The medicaments manufactured and used in accordance with the present invention are particularly useful in the treatment or prevention of ischemia in the brain and especially of dementia caused by ischemia.

Due to the pharmacological profile the medicaments manufactured and used in accordance with the present invention are especially useful in elderly patients.

Citalopram may be prepared by the methods disclosed in U.S. Pat. No. 4,650,884 and the other compounds used in accordance with the invention may be prepared analogueously or by the methods of U.S. Pat. No. 4,136,193. The individual enantiomers of citalopram may be prepared as described in U.S. Pat. No. 4,943,590 and enantiomers of the other compounds of Formula I may be prepared by similar methods.

The acid addition salts of the compounds may be prepared by methods known in the art. The base is reacted with either the calculated amount of acid in a water miscible solvent, such as acetone or ethanol, with subsequent isolation of the salt by concentration and cooling or with an excess of the acid in a water-immiscible solvent, such as ethylether, ethylacetate, or dichloromethane, with the salt separating spontaneously.

The medicaments prepared and used in accordance with the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives, etc. may be used provided that they are compatible with the active ingredients.

Solutions for injections may be prepared by dissolving the active ingredient and possible additives in a part of the solvent for injection, preferably sterile water, adjusting the solution to the desired volume, sterilization of the solution and filling in suitable ampules or vials. Any suitable additive conventionally used in the art may be added, such as tonicity agents, preservatives, antioxidants, etc.

The present compounds and their non-toxic acid addition salts may also be used in combination with other active ingredients, such as neuroleptics, thymoleptics, analgetics, etc.

TOXICITY STUDY

In toxicity studies male and female SD rats ranging in weight from 170 g to 200 g were used one day after fasting. Citalopram was dissolved in water and administered orally. Symptoms were observed for one week after citalopram administration. Even when citalopram was administered at a dose of 350 mg/kg no deaths were observed and accordingly it was obvious that citalopram has a very good safety profile.

PHARMACOLOGICAL TESTS

Ischemia-Induced Hippocampal Death in Gerbils

The overall objective of the study was to investigate the effects of citalopram on hippocampal lesions induced by ischemia in Mongolian gerbils.

Methods

Test compounds were administered intraperitoneally to Male Mongolian gerbils 30 min before carotid occlusion. Carotid occlusion time was 5 min. Seven days after recovery, the animals were killed, brains removed, sectioned and surviving neurons were counted along CA1 in the hippocampus.

Results

As is shown in Table 1, citalopram (20 mg/kg) had a weak but non-significant protective effect against neuronal lesions. The higher dose of this compound (40 mg/kg) showed a significant ($p<0.05$) protective effect against neuronal lesions. Ketamine (100 mg/kg) showed significant ($p<0.01$) protective effect.

TABLE 1

| | Effects on ischemia induced hippocampal neuronal damage in gerbils | | | | |
|---|---|---|---|---|---|
| | Dose | | Survival neurons/mm | | |
| Drug | (mg/kg i.p.) | Gerbils used | mean | S.E. | p |
| Vehicle | — | 10 | 12.8 | 2.6 | |
| Citalopram | 20 | 12 | 38.0 | 18.5 | N.S. |
| Citalopram | 40 | 11 | 95.8 | 27.9 | <0.05 |
| Ketamine | 100 | 8 | 174.5 | 25.7 | <0.01 |

Statistical analysis was carried out according to Dunnett's t-tests vs vehicle group.

Passive Avoidance in Ischemic Gerbils

The test employed was step-down passive avoidance in gerbils treated with test compounds prior to occlusion of carotid arteries followed by acquisition trial (training phase).

Methods

Test compounds were administered intraperitoneally to gerbils 30 min prior to carotid occlusion or ketamine was administered intraperitoneally 10 min prior to carotid occlusion. The gerbils were anesthetized with 2% halothane contained in a mixture of 70% nitrogen and 30% oxygen. The right and left common carotid arteries were occluded for 5 min. The gerbils were trained for 5 min in a step-down type passive avoidance chamber (16×16×20 cm) two days after induced ischemia. Each gerbil was placed on a safety platform (6×16×20 cm) in the chamber and received a series of mild foot shocks (0.1 mA for 3 sec every 6 sec), when the gerbil stepped down to a floor made of metal rods. Gerbils were returned to the safety platform for testing 24 hrs later and their step-down latencies to the grid floor were recorded (max. 60 sec).

Results

Ischemia did not alter step-down latency measured during the training phase. Step-down latency during the training phase was not significantly modified in the gerbils treated with test compound.

Step-down latency in the testing phase was significantly decreased between ischemic control and sham operated gerbils. Citalopram (20 mg/kg) and ketamine (120 mg/kg) significantly increased the latency of ischemic gerbils. But the latency in indeloxazine (40 mg/kg) treated gerbils was not significantly different from that in ischemic control gerbils.

TABLE 2

Effect on passive avoidance in ischemic gerbils

| Drug | Dose (mg/kg i.p.) | Number of gerbils | Ischemic treatment | Step-down latency [log(sec)] Mean | S.E. |
|---|---|---|---|---|---|
| Saline (sham) | — | 15 | — | 1.471 | 0.075*** |
| Saline (control) | — | 20 | + | 0.953 | 0.116 |
| Citalopram | 20 | 7 | + | 1.386 | 0.083** |
| Indeloxazine | 40 | 6 | + | 1.085 | 0.244 |
| Ketamine | 120 | 9 | + | 1.348 | 0.100* |

*p < 0.05,
**p < 0.01,
***p < 0.001 (vs Saline control, by Student's t-test)

Brain Ischemia-Induced Death in Mice

Materials

Male ICR MICE (Charles River) weighing 30-40 g were used after they were fasted for 1 day.

Method

Test compounds were administered intraperitoneally to the mice 30 min prior to permanent ligation of bilateral common carotid arteries under conscious condition. Surviving mice were observed over 4 hrs.

Results

Citalopram (30 mg/kg) significantly prevented ischemia-induced death both 2 hrs and 4 hrs after bilateral carotid arterial ligation. Ifenprodil (30 mg/kg), however, did not significantly increase survival rate 4 hrs after ligation, although it showed significantly increased survival rate 2 hrs after the ligation.

TABLE 3

Effect on ischemia-induced death in bilateral carotid arterial ligation (BCAL) in mice

| Drug | Dose (mg/kg, p.o.) | Number of mice | Survival rate (%) 2 hr after BCAL | 4 hr after BCAL |
|---|---|---|---|---|
| Saline | — | 30 | 23 | 17 |
| Citalopram | 30 | 30 | 50* | 43* |
| Saline | — | 30 | 13 | 7 |
| Ifenprodil | 30 | 30 | 47** | 20 |

*p < 0.05,
**p < 0.01 (Chi-square test vs each Saline)

KCN-Induced Coma in Mice

Methods

Male mice (Crj:ICR) weighing 20-30 g were used. The mice were fasted for one day. The drugs, dissolved in saline, were injected intraperitoneally. 30 min after the injection, KCN, dissolved in saline, was injected intravenously at a dose of 1.3 mg/kg. The duration of disappearance of righting reflex was measured as coma time.

Results

Intraperitonal injection of citalopram significantly reduced coma time at a dose of 10 mg/kg. Indeloxazine at a dose of 20 mg/kg also significantly reduced the coma time.

TABLE 4

Effects of intraperitoneal injection of citalopram on KCN-induced coma in mice

| Drug | Dose (mg/kg, i.p.) | Number of mice | Coma time (sec) Mean | S.E. |
|---|---|---|---|---|
| Vehicle | — | 16 | 55.9 | 8.8 |
| Citalopram | 1.25 | 15 | 38.5 | 4.2 |
| Citalopram | 2.5 | 15 | 33.2 | 10.0 |
| Citalopram | 5 | 16 | 35.0 | 8.2 |
| Citalopram | 10 | 16 | 27.4 | 6.9* |
| Indeloxazine | 20 | 17 | 13.8 | 3.7** |

*P < 0.05,
**P < 0.01, Significantly different from values of vehicle control (Dunnett's t-test).

Carbon Dioxide-Induced Amnesia in Rats (Passive Avoidance Test)

The test employed was a one-trial passive avoidance test in rats, using carbon dioxide asphyxiation to induce amnesia.

Methods

Female Sprague-Dawley (CD) rats (A. Tick & Son Ltd.) in the body weight range 160-180 g were used for the study.

The one-trial passive avoidance apparatus consisted of a 32×32×32 cm chamber with opaque walls and a metal grid floor. A 6 cm wide, 25 cm long runway protruded from the front wall of the chamber. The runway was illuminated while the chamber was dark. When placed on the runway, a rat could enter the chamber through a 6×6 cm opening. A scrambled footshock could be delivered through the metal grid floor of the chamber.

On the first day of the experiment, the rats received three pre-treatment training trials, during which each animal was placed on the end of the runway and the time taken to enter the chamber (the 'step-through' latency) was determined.

On the second day of the experiment, groups of 10 animals were treated p.o. with test compound dissolved in saline or with saline.

One hour after administration, an acquisition trial was performed. This was similar to a training trial, except that the rats received a footshock of 1.0 mA for 10 sec. commencing 10 sec after entering the chamber. Immediately after the application of the footshock the animals were subjected to amnesic treatment.

Amnesic treatment consisted of placing the rats in a box filled with carbon dioxide until respiratory arrest occurred; the rats were then revived by artificial respiration. 24 Hours after the acquisition trial, a single retrieval trial was given to each rat and the time taken to enter the chamber ('step-through' latency) was recorded for each animal.

If a rat did not enter the chamber within 180 seconds it was taken from the runway.

Results

There were no significant differences between the time of entry ('step-through' latency) of rats dosed with either vehicle, citalopram or piracetam, thus indicating that at oral doses of 40 or 1000 mg/kg, these compounds did not induce marked muscle incoordination of CNS effects of sufficient magnitude to modify entry times. The amnesic effect of carbon dioxide has been clearly demonstrated in this study. In those rats receiving footshock, but no drug treatment, treatment with carbon dioxide asphyxiation caused a decrease in 'step-through' latency.

Oral administration of citalopram at all doses tested caused dose-related increases in the group mean 'step-through' times, which in most cases were statistically significant when compared to the saline-treated control group using Student's t-test. At the 2 highest doses tested (i.e., 20 and 40 mg/kg), a marked and highly significant increase in time was observed.

As expected, piracetam treatment gave statistically significantly longer 'step-through' latencies.

TABLE 5

Effects of oral administration of citalopram on carbon dioxide-induced amnesia in rats.

| Drug | Dose (mg/kg; p.o.) | CO2 Treatment | Number of animals | Latency (sec) |
|---|---|---|---|---|
| Saline | — | — | 10 | 119.6*** |
| Saline | | + | 10 | 0.8 |
| Citalopram | 5 | + | 10 | 31.2 |
| Citalopram | 10 | + | 10 | 77.2** |
| Citalopram | 20 | + | 10 | 114.3*** |
| Piracetam | 300 | + | 10 | 108.8*** |

**p < 0.01,
***p < 0.001, significantly different from values of relevant control group (Students t-test).

In Vitro Platelet Aggregation

Methods

The test was performed with fresh human platelets. The drugs were diluted in physiological saline to give a solution at a concentration ten times that of the final concentration. The drug was added to the platelets and incubated at 37° C. for 15 min. and then platelet aggregation was induced by the addition of collagen (10 microgram/ml).

Results

Citalopram at a final concentration of 100 microgram/ml inhibited the aggregation of human platelet induced by collagen by 58%. The same concentration of indeloxazine revealed weaker inhibitory effect (8%) than citalopram did on the aggregation by collagen.

Ex Vivo Platelet Aggregation

Effect on collagen-induced platelet aggregation using blood of rats administered orally with citalopram was investigated.

Materials

Male Wistar rats (Charles River) in the body weight range 350–400 g were used.

Methods

One hour after oral dosing the rats were lightly anesthetized with ether and blood was collected by cardiac puncture. Nine ml of the blood was mixed with 1 ml of 3.8% sodium citrate and platelet rich plasma (300000 platelets/cmm) was prepared. At the end of the incubation period at 37° C. for 2 min. effects of addition of 10 microgram/ml collagen on platelet aggregation were determined.

Results

A moderate inhibition of collagen-induced aggregation was noted following citalopram at 30 mg/kg (60.4%). At doses of 10 mg/kg only slight inhibition of collagen-induced aggreagation was noticed (16.7%).

TABLE 6

Effect on platelet aggregation ex vivo in rats.

| Drug | Dose (mg/kg, p.o.) | Number of rats | Mean (%) | S.D. (%) | [% Change from control] |
|---|---|---|---|---|---|
| Vehicle | — | 12 | 54.6 | 27.3 | [—] |
| Citalopram | 10 | 8 | 45.5 | 16.0 | [−16.7] |
| Citalopram | 30 | 8 | 21.6 | 21.6** | [−60.4] |

S.D.: Standard deviation.
Statistical significance using analysis of variance of treatment groups as compared to vehicle treated groups,
**P < 0.01.

It appears from the foregoing Ischemia Induced Hippocampal Death Test that the compound according to the invention tested shows improving effect on neuronal lesion. The Passive Avoidance Test is Ischemic gerbils indicates improving effect on memory following ischemic attack, the Brain Ischemia-Induced Death Test in mice indicate effect on survival rate following ischemic attack, the KCN-induced Coma test in mice indicates improving effect following anoxia, and the Carbondioxide-Induced Amnesia Test in rats show positive effect on amnesia.

The results of the in vitro and the in vivo Platelet Aggregation Tests show inhibiting effects on platelet aggregation.

Clinical Test

In a group of depressed patients having concomitant dementia, it was observed that cognitive functions improved after treatment with compounds of the general Formula I but not after treatment with placebo. Accordingly, compounds of general Formula I clinically have memory improving effect in patients having dementia which may not only be of cerebrovascular origin but also may result from chronic organic reactions such as neurodegenerative disorders. This is in contradiction to the earlier study of Nyth et al. mentioned above (Nyth, A. L. et al. "The effect of citalopram in dementia disorders", presentation at CINP, August 1988).

FORMULATION EXAMPLES

The following examples show typical formulations of the medicaments manufactured in accordance with the invention.

| 1) Tablets containing 0.5 milligram of citalopram calculated as the free base: | |
|---|---|
| Citalopram | 100 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |
| 2) Tablets containing 1 milligram of citalopram calculated as the free base: | |
| Citalopram | 50 mg |

| -continued | |
|---|---|
| Lactose | 16 mg |
| Potato starch | 45 mg |
| Sacc'harose | 106 mg |
| Sorbitol | 6 mg |
| Talcum | 9 mg |
| Gelatine | 4 mg |
| Povidone | 3 mg |
| Magnesium stearate | 0.6 mg |
| 3) Syrup containing per milliliter: | |
| Citalopram | 5.0 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |
| 4) Solution for injection containing per milliliter: | |
| Citalopram | 50 mg |
| Acetic acid | 17.9 mg |
| Sterile water | ad 1 ml |
| 5) Solution for injection containing per milliliter: | |
| Citalopram | 10 mg |
| Sorbitol | 42.9 mg |
| Acetic acid | 0.63 mg |
| Sodium hydroxide | 22 mg |
| Sterile water | ad 1 ml |

We claim:

1. A method for the treatment of dementia cognitive disorders, or amnesia associated with and cerebrovascular disorders in a patient in need thereof comprising the step of administering an amount of a 1-[3-(dimethylamino)propyl]-1-phenylphthalane of the formula

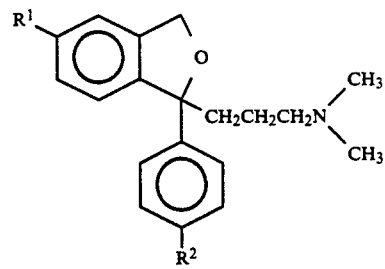

Formula I wherein $R^1$ and $R^2$ each are selected from the group consisting of halogen, trifluoromethyl, cyano and R—CO—, wherein R is an alkyl radical with 1 to 4 C-atoms inclusive a, or a pharmaceutically-acceptable acid addition salt thereof which is effective for such purpose to the said patient.

2. A method according to claim 1 wherein the cerebrovascular disorder is caused by cerebral infarction, cerebral hemorrhage, cerebral arteriosclerosis, subarachnoid hemorrhage, cerebral thrombosis, or cerebral embolism.

3. A method according to claim 2 wherein the disorder is ischemia.

4. A method according to claim 2 wherein the disorder is amnesia associated with ischemia.

5. A method according to claim 2 wherein the disorder is Vascular or Multiinfarct dementia.

6. A method according to claim 1 wherein the disorder is dementia of the Alzheimer's type.

7. A method according to claim 1 wherein the compound of Formula I is citalopram or a pharmaceutically-acceptable acid addition salt thereof.

* * * * *

UNITED STATES PATENT AND TRADEMARK OFFICE
CERTIFICATE OF CORRECTION

PATENT NO. : 5,296,507
DATED : Mar. 22, 1994
INVENTOR(S) : Yoshiaki Tanaka, Naomi Kobayashi, Tadashi Kurimoto, Yugo Ikeda It is certified that error appears in the above-indentified patent and that said Letters Patent is hereby corrected as shown below:

```
Title Page, [54],; "TREATMENT OF CERBROVASCULAR DISORDERS"
     should read -- TREATMENT OF CEREBROVASCULAR DISORDERS --.
Column 1, approximately lines 33-34; "centrally active" should
     read -- centrally-active --.
Column 2, line 43; "dementia or" should read --dementia, or --.

Column 3, line 50; "water miscible" should  read
     -- water-immiscible --.
Column 8, line 20; "**P < 0.01." should read
     -- **:P<0.01. --.
Column 8, line 25; "Test is" should read -- Test in --.
Column 9, line 30,31; "of dementia cognitive disorders,
     or amnesia associated with and" should read
     -- of cognitive disorders or amnesia
     associated with dementia, --.

Column 9, line 32; insert a comma after "disorders".
Column 10, line 17; "inclusive a," should read --inclusive,--.
Column 10, line 18; insert a comma after "thereof".
Column 10, line 19; insert a comma after "purpose".
```

Signed and Sealed this

Twentieth Day of September, 1994

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,296,507

DATED : Mar. 22, 1994

INVENTOR(S) : Yoshiaki Tanaka, Naomi Kobayashi, Tadashi Kurimoto, Yugo Ikeda

It is certified that error appears in the above-indentified patent and that said Letters Patent is hereby corrected as shown below:

Title Page, [54],; "TREATMENT OF CERBROVASCULAR DISORDERS" should read -- TREATMENT OF CEREBROVASCULAR DISORDERS --.

Column 1, approximately lines 33-34; "centrally active" should read -- centrally-active --.

Column 2, line 43; "dementia or" should read --dementia, or --.

Column 3, line 50, "water miscible" should read -- water-miscible --.

Column 8, line 20; "P < 0.01." should read -- :P<0.01. --.

Column 8, line 25; "Test is" should read -- Test in --.

Column 9, line 30,31; "of dementia cognitive disorders, or amnesia associated with and" should read -- of cognitive disorders or amnesia associated with dementia, --.

Column 9, line 32; insert a comma after "disorders".

Column 10, line 17; "inclusive a," should read --inclusive,--.

Column 10, line 18; insert a comma after "thereof".

UNITED STATES PATENT AND TRADEMARK OFFICE
CERTIFICATE OF CORRECTION

PATENT NO. : 5,296,507
DATED : March 22, 1994
INVENTOR(S) : Yoshiaki Tanaka, et al.

It is certified that error appears in the above-indentified patent and that said Letters Patent is hereby corrected as shown below:

Column 10, line 19, insert a comma after "purpose".

This certificate supersedes Certificate of Correction issued September 20, 1994.

Signed and Sealed this

Thirteenth Day of June, 1995

*Attest:*

BRUCE LEHMAN

*Attesting Officer*         *Commissioner of Patents and Trademarks*